(12) United States Patent  
Maxwell

(10) Patent No.: US 8,934,705 B2  
(45) Date of Patent: Jan. 13, 2015

(54) PERSISTENT FEATURE DETECTION

(75) Inventor: Ian Andrew Maxwell, New South Wales (AU)

(73) Assignee: BT Imaging Pty Ltd, Surry Hills (AU)

( * ) Notice: Subject to any disclaimer, the term of this patent is extended or adjusted under 35 U.S.C. 154(b) by 151 days.

(21) Appl. No.: 13/813,765

(22) PCT Filed: Aug. 8, 2011

(86) PCT No.: PCT/AU2011/000997  
§ 371 (c)(1),  
(2), (4) Date: Feb. 1, 2013

(87) PCT Pub. No.: WO2012/019219  
PCT Pub. Date: Feb. 16, 2012

(65) Prior Publication Data  
US 2013/0129187 A1    May 23, 2013

(30) Foreign Application Priority Data  
Aug. 9, 2010   (AU) .................................. 2010903558

(51) Int. Cl.  
*G06K 9/00* (2006.01)  
*G06K 9/46* (2006.01)  
*G01N 21/95* (2006.01)  
*H01L 31/18* (2006.01)  
*H01L 21/66* (2006.01)

(52) U.S. Cl.  
CPC .............. *G06K 9/4671* (2013.01); *G01N 21/95* (2013.01); *H01L 31/1876* (2013.01); *G01N 21/9501* (2013.01); *H01L 22/12* (2013.01); *Y02E 10/50* (2013.01)

USPC ........... 382/141; 382/145; 382/149; 382/151; 348/86; 348/125

(58) Field of Classification Search  
USPC ............ 382/141, 143, 145, 149, 151; 348/86, 348/92, 125, 126  
See application file for complete search history.

(56) References Cited

U.S. PATENT DOCUMENTS

| | | | |
|---|---|---|---|
| 6,895,109 B1 * | 5/2005 | Schemmel et al. ........... | 382/149 |
| 7,388,979 B2 * | 6/2008 | Sakai et al. .................... | 382/149 |
| 7,485,858 B1 * | 2/2009 | Obara et al. ................... | 250/306 |
| 7,673,281 B2 * | 3/2010 | Yamanaka et al. .............. | 716/53 |
| 7,711,178 B2 * | 5/2010 | Sakai et al. .................... | 382/151 |
| 7,873,202 B2 * | 1/2011 | Kurihara et al. .............. | 382/141 |
| 8,385,627 B2 * | 2/2013 | Toba et al. .................... | 382/145 |

FOREIGN PATENT DOCUMENTS

| | | |
|---|---|---|
| JP | 2000-195915 A | 7/2000 |
| JP | 2001-050712 A | 2/2001 |
| JP | 2007-067102 A | 3/2007 |
| WO | 2007/041758 A1 | 4/2007 |
| WO | 2007/128060 A1 | 11/2007 |

(Continued)

*Primary Examiner* — Yosef Kassa  
(74) *Attorney, Agent, or Firm* — Mattingly & Malur, PC

(57) ABSTRACT

Methods are presented for improved detection of persistent or systematic defects induced during the manufacture of a product. In particular, the methods are directed to the detection of defects induced systematically in the manufacture of photovoltaic cells and modules. Images acquired from a number of samples are combined, enhancing the systematic defects and suppressing random features such as variations in material quality. Once a systematic defect is identified, steps can be taken to locate and rectify its cause.

30 Claims, 7 Drawing Sheets

(56) References Cited

FOREIGN PATENT DOCUMENTS

| WO | 2009/026661 | A1 | 3/2009 |
| WO | 2009/121133 | A1 | 10/2009 |
| WO | 2011/079353 | A1 | 7/2011 |
| WO | 2011/079354 | A1 | 7/2011 |

* cited by examiner

PERSISTENT FEATURE DETECTION

FIELD OF THE INVENTION

The present invention relates to methods for detecting systematic defects induced in products by one or more stages of a process used to manufacture the products. The invention has been developed primarily for detecting systematic process-induced defects such as cracks in photovoltaic wafers, cells and modules, however it will be appreciated that the invention is not limited to this particular field of use.

RELATED APPLICATIONS

The present application claims priority from Australian provisional patent application No 2010903558, the contents of which are incorporated herein by reference.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

In a process for the volume manufacture of products such as photovoltaic cells, there is the potential for systematic manufacturing errors to cause defects in the product. For example a piece of foreign material lodged in a print screen can cause a defect such as a crack, scratch or stain in a large number of photovoltaic cells until it is detected and removed. The sooner such problems can be detected and corrected, the less the economic impact.

Irrespective of the type of product being manufactured however, it can be difficult to distinguish process-induced defects from features that are inherent in the product material. In the context of photovoltaic cells manufactured from multicrystalline silicon for example, and as described in Japanese patent application No JP2007-067102 A, it can be difficult for optical imaging techniques (typically involving reflection or transmission of light in the visible or infrared spectral regions) to distinguish process-induced defects such as stains from the grains or grain boundaries of the multicrystalline material.

Photoluminescence (PL) imaging has been proposed as a convenient and fast technique for assessing the quality of semiconductor material being fed into a photovoltaic cell line, and for monitoring the photovoltaic cells throughout their manufacture process and onwards into module assembly, see generally published PCT patent application Nos WO 2007/041758 A1, WO 2007/128060 A1, WO 2009/026661 A1, WO 2009/121133 A1, WO 2011/079353 A1 and WO 2011/079354 A1. After electrical contacts have been printed, luminescence can be generated additionally or alternatively by electrical excitation (electroluminescence, EL). In particular, luminescence (PL and/or EL) from multicrystalline or monocrystalline silicon has been shown to deliver information about many material and electrical properties that can influence the performance of photovoltaic cells, including dislocations, atomic impurities, inclusions, shunts, contact resistance of metal lines, and cracks. Since grain boundaries also influence the electron-hole recombination responsible for the luminescence emission, they can also show up in luminescence images. However in this wealth of information it can be difficult to distinguish one type of feature from another. Image processing algorithms are useful to some extent, working on the principle that different types of features have different dimensional patterns, but these algorithms cannot generally distinguish process-induced defects from intrinsic material features. Similar difficulties apply to other characterisation techniques including optical (reflection or transmission) imaging.

SUMMARY OF THE INVENTION

It is an object of the present invention to overcome or ameliorate at least one of the disadvantages of the prior art, or to provide a useful alternative. It is an object of a preferred form of the present invention to provide improved methods for detecting persistent process-induced effects in a photovoltaic cell production line.

A first aspect of the present invention provides a method for detecting systematic features in products being manufactured on a process line, said method comprising the steps of:
 (a) acquiring images of a plurality of said products, each image being of substantially the same area on each of said products;
 (b) combining said images to obtain a super-image;
 (c) processing said super-image to identify regions with strong signals; and
 (d) identifying said regions as being indicative of systematic features in said products.

A second aspect of the present invention provides a method for detecting systematic features in products being manufactured on a process line, said method comprising the steps of:
 (a) acquiring images of a plurality of said products, each image being of substantially the same area on each of said products;
 (b) combining said images to obtain a super-image;
 (c) processing said super-image to identify regions with strong signals;
 (d) comparing said regions with known features in said area; and
 (e) identifying those of said regions that do not correspond to said known features as being indicative of systematic features in said products.

A third aspect of the present invention provides a method for detecting systematic features in products being manufactured on a process line, said method comprising the steps of:
 (a) acquiring images of a plurality of said products, each image being of substantially the same area on each of said products;
 (b) correcting said images to remove known features in said area,
 (c) combining the corrected images to obtain a super-image;
 (d) processing said super-image to identify regions with strong signals; and
 (e) identifying said regions as being indicative of systematic features in said products.

A fourth aspect of the present invention provides a method for detecting process-induced defects in products being manufactured on a process line, said method comprising the steps of:
 (a) acquiring images of corresponding areas of a plurality of said products;
 (b) cumulating said images to produce a cumulative image; and
 (c) identifying signals in said cumulative image which exceed a predetermined threshold thereby determining said process-induced defects.

A fifth aspect of the present invention provides a method for detecting process-induced defects in products being manufactured on a process line, said method comprising the steps of:

(a) acquiring images of corresponding areas of a plurality of said products;
(b) cumulating said images to produce a cumulative image;
(c) identifying signals in said cumulative image which exceed a predetermined threshold thereby determining one or more defect candidates; and
(d) excluding from said candidates any known features, thereby determining said process-induced defects.

A sixth aspect of the present invention provides a method for detecting process-induced defects in products being manufactured on a process line, said method comprising the steps of:

(a) acquiring images of corresponding areas of a plurality of said products;
(b) correcting said images by removing signals in each said image which correspond to any known features;
(c) cumulating said images to produce a cumulative image; and
(d) identifying signals in said cumulative image which exceed a predetermined threshold thereby determining said process-induced defects.

A seventh aspect of the present invention provides, in a process line for manufacturing products, a method for detecting systematic features in products being manufactured on said process line, said method comprising the steps of:

(a) acquiring images of a plurality of said products, each image being of substantially the same area on each of said products;
(b) combining said images to obtain a super-image;
(c) processing said super-image to identify regions with strong signals; and
(d) identifying said regions as being indicative of systematic features in said products.

An eighth aspect of the present invention provides, in a process line for manufacturing products, a method for detecting process-induced defects in products being manufactured on said process line, said method comprising the steps of:

(a) acquiring images of corresponding areas of a plurality of said products;
(b) cumulating said images to produce a cumulative image; and
(c) identifying signals in said cumulative image which exceed a predetermined threshold thereby determining said process-induced defects.

The first to eighth aspects share a number of preferments. Preferably the images are acquired from substantially identical corresponding areas of the products. In one embodiment, the images which are acquired are of adjacent products in the process line, which images are then combined or cumulated and analysed. In another embodiment, the images which are acquired are of 3, 4, 5, 6, 7, 8, 9, 10, 15, 20, 25, 50, 100, 200, 300, 400, 500 or 1,000 adjacent products in the process line, which images are then cumulated and analysed. Preferably the images are a 'rolling' set of images, meaning that as a new image is acquired the first-acquired image is withdrawn from the set of images being cumulated and analysed. In another embodiment, as a set of 5, 10, or 20 images are acquired the first-acquired 5, 10, or 20 images are withdrawn from the set of images being cumulated and analysed. In other embodiments, the images which are acquired are of a product and the third subsequently-produced product, or the fourth, fifth, or sixth subsequently-produced product. Preferably the images which are acquired are of the $n^{th}$ subsequently-produced product; wherein n is an integer from 2, 3, 4, 5, 6, 7, 8, 9, 10 etc. In related embodiments, the images which are acquired are of the $x^{th}$ subsequently-produced product; wherein x is an integer from 2, 4, 6, 8, 10 etc. In yet other embodiments, the images which are acquired are of a random selection of products.

It will be appreciated that the images comprise at least one signal, and more preferably a signal map. The signals are preferably produced from photoluminescence or electroluminescence of the products, which are preferably photovoltaic wafers, cells or modules. However, it will be appreciated that optical (reflection or transmission in the visible or infrared spectral regions) imaging is also possible to produce the image/signal map.

It will be appreciated that known features, if present, are generally inherent or intrinsic to the product being assessed, and can be thought of as characteristics of the product. These inherent features or characteristics may for example be selected from one or more of the group consisting of: dislocations, atomic impurities, inclusions, shunts, metal lines, contact resistance of metal lines, cracks, grain boundaries, surface stains etc, and may be desirable aspects of the product (e.g. metal lines on a photovoltaic cell) or undesirable aspects (e.g. impurity-rich regions).

The process-induced or systematic features tend to be cracks, surface stains, shunts, poor electrical contacts, broken electrical traces etc, and can be contrasted with inherent features in that they are generally unexpected. Systematic features may also include lateral variations in doping density or carrier density/lifetime that may indicate a problem with a process step such as impurity gettering, SiN passivation, rear surface metallisation or furnace firing.

The images which are acquired are combined or cumulated to produce a cumulative image, or a 'super-image', preferably by summing, averaging or obtaining a median. The cumulative or super-image may comprise a pixel-by-pixel comparison of the plurality of acquired images, preferably a summation of the intensity of the corresponding pixels from each image. It may also be required that the images are aligned before being combined or cumulated, for example by slight adjustment of the image by rotation and/or translation, since there will be some product-to-product variation in the captured images. To explain, slight movements in the products during processing on the process line may cause the images to be slightly askew from each other, and so some correction of the image, e.g. by a reference point within the image, may be required. The cumulation or combining process may include monitoring statistical variances from expected values for regions of the images.

In preferred embodiments the signals in the cumulative image or super-image are compared with a predetermined threshold level that may be determined by a number of methods, for example as a percentage or absolute off-set above an average signal level in the cumulative image or super-image. Alternatively the threshold level can be set by an operator.

Preferably, the method is performed at multiple stages in the process line, to identify stages in the process line where the systematic features might be introduced. The products are preferably photovoltaic wafers, cells or modules. More preferably, the systematic or process-induced features are cracks in the photovoltaic wafers, cells or modules. Preferably, the cumulative image or super-image is further processed to determine an average signal level, or a background signal level in portions away from the regions with strong signals, and the average or background signal level used to predict the performance of the photovoltaic wafers, cells or modules.

In preferred forms the method further comprises the step of identifying the type or nature of the systematic features. The method may further comprise the step of taking action to remove the process cause of said systematic features.

A ninth aspect of the present invention provides an apparatus when used to implement the method according to any one of the first eight aspects.

An tenth aspect of the present invention provides an article of manufacture comprising a computer usable medium having a computer readable program code configured to implement the method according to any one of the first eight aspects, or to operate the apparatus according to the ninth aspect.

BRIEF DESCRIPTION OF THE DRAWINGS

Benefits and advantages of the present invention will become apparent to those skilled in the art to which this invention relates from the subsequent description of exemplary embodiments and the appended claims, taken in conjunction with the accompanying drawings:

DETAILED DESCRIPTION

Figure 1A:
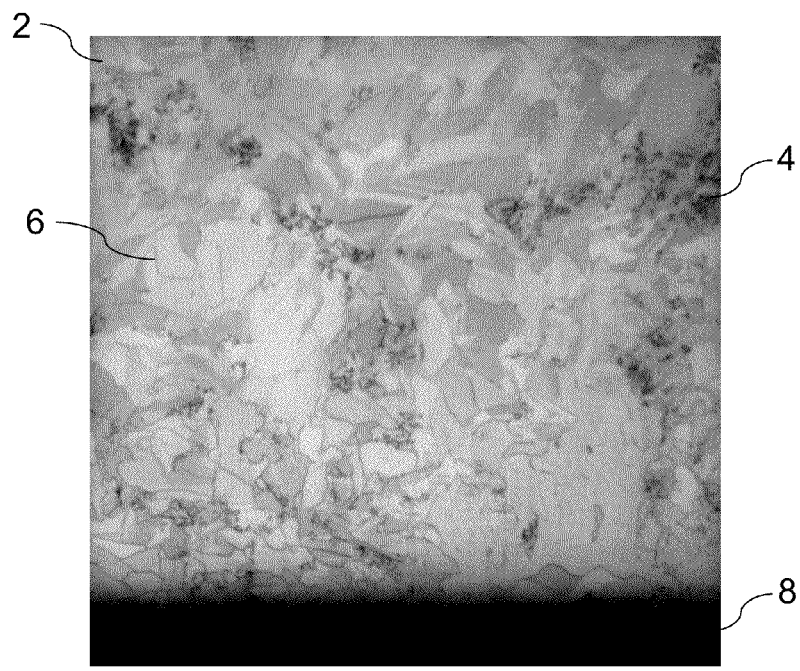
FIGS. 1A and 1B show PL images of a multicrystalline silicon wafer and a monocrystalline silicon wafer respectively, showing some features of interest to photovoltaic cell manufacturers.

The present invention relates to methods for detecting systematic defects induced in products by one or more stages of a process line on which the products are manufactured. The invention will be described for the particular application of detecting systematic process-induced defects such as cracks in photovoltaic wafers, cells and modules, but the invention is not limited to this particular field of use.

As mentioned previously, many material and electrical properties of semiconductor materials can be identified with known characterisation techniques. For example PL and EL imaging can provide information on the occurrence and distribution of many features including dislocations, atomic impurities, inclusions, shunts, contact resistance of metal lines, cracks and grain boundaries. Reflection imaging can reveal surface stains, cracks and grain boundaries, while infrared transmission can provide information on the three-dimensional distribution of cracks and inclusions. Some of these features, including dislocations, impurities, inclusions and grain boundaries, are intrinsic to the material and not process-induced. On the other hand, features such as cracks, shunts, surface stains, poor electrical contacts and broken electrical traces, all of which can degrade the performance of photovoltaic cells and modules, can be induced during the manufacture of cells or modules. In some cases such features will occur randomly, but in other cases they may occur repeatedly in many or all of the products. These systematic (or 'persistent') features are usually indicative of a fault in the process line, but in some instances can indicate a defective wafer feedstock. Either way, it is usually advantageous to identify and rectify the cause as soon as possible, especially if the persistent features are or have the potential to become deleterious to performance of the product.

The methods of present invention provide improved detection of persistent features, and are applicable to any imaging technique capable of detecting the type of feature in question. Optical reflections from a sample are affected by factors including surface roughness and other surface morphology, absorption at selected wavelengths and refractive index variations; consequently for photovoltaic cells and wafers optical reflection imaging may be able to detect cracks, surface etching and texture variations, anti-reflection coating variations and surface stains or particles. The photoluminescence response from a photovoltaic cell or wafer is sensitive to many or all of the optically visible features, as well as minority carrier density/lifetime and background doping density. Therefore PL imaging can be useful for detecting a large number of features including physical defects such as cracks, and lateral variations in doping density or carrier density/lifetime that may indicate a problem with a process step such as impurity gettering, SiN passivation, rear surface metallisation or furnace firing.

The inventive methods rely on the fact that features such as cracks systematically induced by a defective stage in a manufacturing process tend to occur in the same or similar positions in each sample. If images acquired from the same area of a large number of samples (from say five to many hundreds) are combined to form a 'super-image', features with random or statistical distributions (such as dislocations, impurities, inclusions and grain boundaries) will be suppressed in the super-image, while a systematic feature (such as a crack caused by a piece of foreign material caught in a screen print, or from thermal or mechanical stress on cells during module assembly) will be enhanced. Allowance can also be made for the presence of known, expected or intentional features at predictable locations, such as metal contacts on a photovoltaic cell, crystal grain structures in similar positions in a series of wafers cut from adjacent portions of a brick, or defects already known to be present in all or many of the samples.

Signals from persistent features (e.g. a crack induced at a specific position on numerous photovoltaic cells) will be multiplied many times over to form strong signals in a cumulative or super-image, whilst the 'noise' level of the rest of the sample will become normalised to a mean level, thus allowing easy detection of persistent features by simple image analysis techniques such as edge detection algorithms, preferably including quantification of their severity. The 'strong signals' need not be bright signals among a darker background, and in fact may often be dark signals among a brighter background.

In general, a region with strong signals in an image or super-image is a region where the signal levels are strongly divergent from the signal levels in the remainder of the image or super-image, possibly determined with respect to a threshold level that may for example be set automatically as a percentage or absolute off-set above an average signal level, or operator-definable. Some persistent features, such as metal lines on photovoltaic cells for example, are in fact expected and not considered to be defects, and are preferably removed from the images either before or after the images have been combined.

We note that for multicrystalline silicon wafers for example, some inherent features such as grain boundaries and dislocations will generally be in similar positions in wafers cut from adjacent portions of a brick, and hence may be emphasised as persistent features in a super-image, essentially resulting in false positives subject to the sample set size and depending on whether wafers are fed into the process line in the same or similar order as they were cut. The same considerations would also apply to monocrystalline silicon wafers with slip lines. This 'adjacent sample' problem is likely to be indicated if a large and possibly wafer-wide number of persistent features were detected, and in some embodiments can be ameliorated by changing the detection threshold of the persistent feature algorithm. In other embodiments image processing algorithms may be able to distinguish reliably between different types of features, e.g. grain boundaries, dislocations and cracks, enabling the persistent feature algorithm to focus on features that are more likely to be process-induced, e.g. cracks. Alternatively their enhancement can be ameliorated by using a sample set that avoids the 'adjacent sample' problem, e.g. by measuring wafers that are many process unit steps apart to lessen the risk of measuring wafers from the same brick or from similar positions within a brick. In production lines where the as-cut wafer sequence is scrambled or randomised before the wafers enter the line, the 'adjacent sample' problem is unlikely to occur.

Figure 1B:
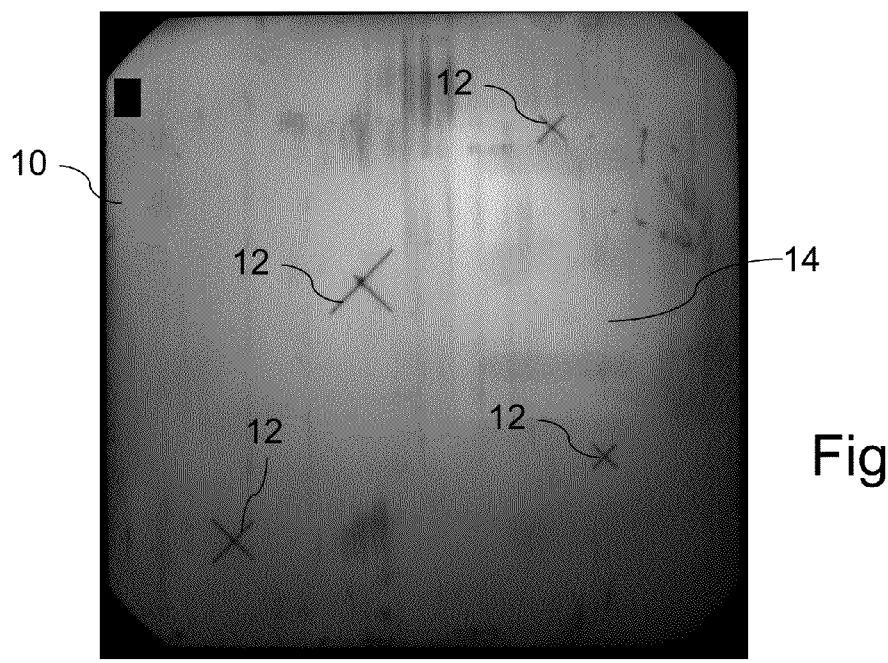

Although the inventive method is applicable to any imaging technique capable of detecting the systematic feature of interest, PL imaging is particularly preferred because of the wide range of features and material properties it can detect. For example while optical imaging and infrared transmission can detect physical features such as cracks and variations in surface texture, they are unable to detect electrical defects such as shunts or poor electrical contacts. In addition, because regions with higher carrier lifetime exhibit stronger PL emission, the 'background' PL signal level, i.e. in areas without persistent defects, will give an operator a moving average of wafer and/or process quality, and thus a measure of likely cell quality. PL imaging is also a non-contact technique, like optical imaging but unlike EL imaging for example, which is an advantage because contacting photovoltaic cells can cause further cracking. PL imaging and optical imaging can also be used to inspect wafers before the formation of electrical contacts. The ability of PL imaging to detect various features of interest to photovoltaic cell manufacturers is demonstrated in FIGS. 1A and 1B. The PL image shown in FIG. 1A, of a multicrystalline silicon wafer 2, reveals a number of recombination active dislocation clusters 4 and grain boundaries 6, and a low lifetime region of impurity-rich silicon 8 along one edge indicating that the wafer was cut from a so-called 'edge brick', adjacent to a crucible wall. The PL image shown in FIG. 1B, of a monocrystalline silicon wafer 10, reveals a number of deliberately induced cracks 12. The large, slightly brighter feature 14 appearing in the FIG. 1B image is a support post visible through the wafer, which has substantial transparency beyond about 1000 nm.

Apparatus for acquiring PL images from a sample typically includes an optical source of wavelength and intensity suitable for generating photoluminescence from the sample material, a camera for acquiring images, beam shaping optics in the illumination and imaging paths, and a long pass filter for protecting the camera from the illumination light. Apparatus for acquiring EL images typically includes a source of electrical power for electrically exciting a sample to emit luminescence, a camera for acquiring images, and beam shaping optics in the imaging path. Apparatus for acquiring optical images typically includes an illumination source and a camera. Each apparatus would generally require a processor for calculating and analysing the cumulative or super-images.

In certain embodiments the invention is implemented as follows:

(i) A number of samples (e.g. photovoltaic cells or cell precursors) are illuminated with an optical source of suitable intensity and wavelength to generate photoluminescence. Preferably each sample is measured at the same stage in a process line, and the same area of each sample should be illuminated and imaged. In some embodiments images the entire area of each sample is imaged, while in other embodiments only a selected area of each sample is imaged. If only a selected area is imaged, it should be substantially the same area of each sample. The samples are preferably sequential on the process line, or in a periodic sequence e.g. every tenth sample. Alternatively a random selection of samples is imaged. The light source may for example be a laser with appropriate optics, or preferably an LED array if laser safety requirements are a concern. In the context of a photovoltaic cell process line the illumination may be for a short period of time whilst the sample is temporarily stopped for measurement, or preferably while the sample is still moving if the measurement time is sufficiently short. High intensity illumination sources such as flash lamps are advantageous for rapid measurement of moving samples.

(ii) An appropriate camera is used to measure the PL signal generated from each sample as a result of the illumination. At least one megapixel resolution over a whole cell or cell precursor is preferred for crack detection. Techniques for boosting the signal-to-noise ratio, such as background light minimisation (e.g. a light box) and lock-in detection, can be applied if necessary. The camera may for example be an area camera, with images acquired in a single exposure. Alternatively, the camera may be a line camera or a time delay integration (TDI) camera, with images acquired line-by-line as the samples move along a process line.

(iii) The PL images of the samples, preferably a set of sequential or sequentially periodic samples, are combined to form a 'super-image'. The combining function can for example be summing, averaging or obtaining a median, or it may be some other more complex function. The actual mathematical functions employed can be as simple as summing the camera response (count rate) in each pixel of individual images and reporting a super-image of all the summed pixel counts.

The combining function can have many different forms, from simple signal averaging, to the more complex processing of keeping detailed statistical information about pixel or regional variances across each image. Additionally, it will be evident to those skilled in the art of image processing that the combining can be done in both the spatial domain of pixels or regions, or in the frequency or Fourier domain where Fourier components are separately combined or analysed. In other embodiments, other domains such as Discrete Cosine Transform, Hadamard or Wavelet domains could be utilised.

Additionally, the images may be subject to enhancement filters in accordance with requirements. Where enhancement filters are utilised, complex nonlinear combinations of image information may be utilised. Sophisticated filtering may be applied to the images, utilising process outlined in the standard textbooks such as: 'Digital Image Processing', by Gonzalez and Woods, Addison Wesley Publishing.

The combining process can also include an initial registration process of morphing or translating images so that they are appropriately aligned or correlated.

(iv) The 'super-image' is then processed to identify regions having strong signals, i.e. signals with a strong divergence from an expected value, which are indicative of features present in a substantial number of samples in the set.

(v) Features known to be persistent (e.g. metal grid lines on a photovoltaic cell or grains within a brick) can be independently filtered out, allowing features that are persistent and unexpected (e.g. cracks, chips or stains) to be isolated.

(vi) Further data processing will then note the position and severity of the unexpected persistent features and report this to an operator for action, e.g. to investigate and rectify the cause, and/or be recorded for further checking of the series of samples with this persistent feature in later processing. This step may also include the use of image processing algorithms to identify the nature or type of the persistent feature, e.g. crack or surface stain, possibly with reference to a database of known or expected features in the products.

If the samples have no known persistent features (e.g. high quality monocrystalline photovoltaic wafers before formation of electrical contacts), strong signal regions in the cumulative or super-image can be immediately identified as probable systematic defects.

In an alternative embodiment, individual images can be corrected to remove known persistent features before being cumulated or combined to form the cumulative image or super-image.

Some examples will now be described to illustrate the inventive principles. For ease of presentation of signal intensity versus position, intensity line scans across simulated two-dimensional images of samples will be combined to form representative super-images. In practice however, we envisage that the two-dimensional images will be combined to form a super-image. As noted above, two-dimensional images may be acquired in a single exposure with an area camera or line-by-line with a line camera or TDI camera. It should be understood that a line image is itself an image of a selected area of a sample.

EXAMPLE 1

Figure 2A:
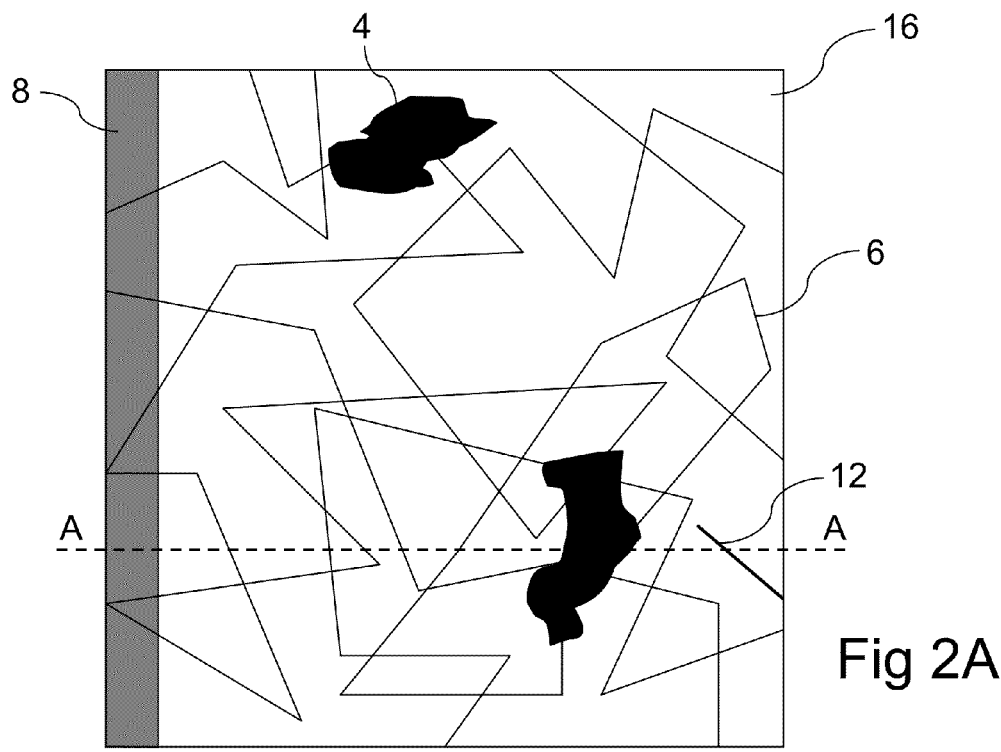
FIGS. 2A and 2B show simulated PL images of two different multicrystalline silicon wafers, where each wafer has a crack.
Figure 2B:
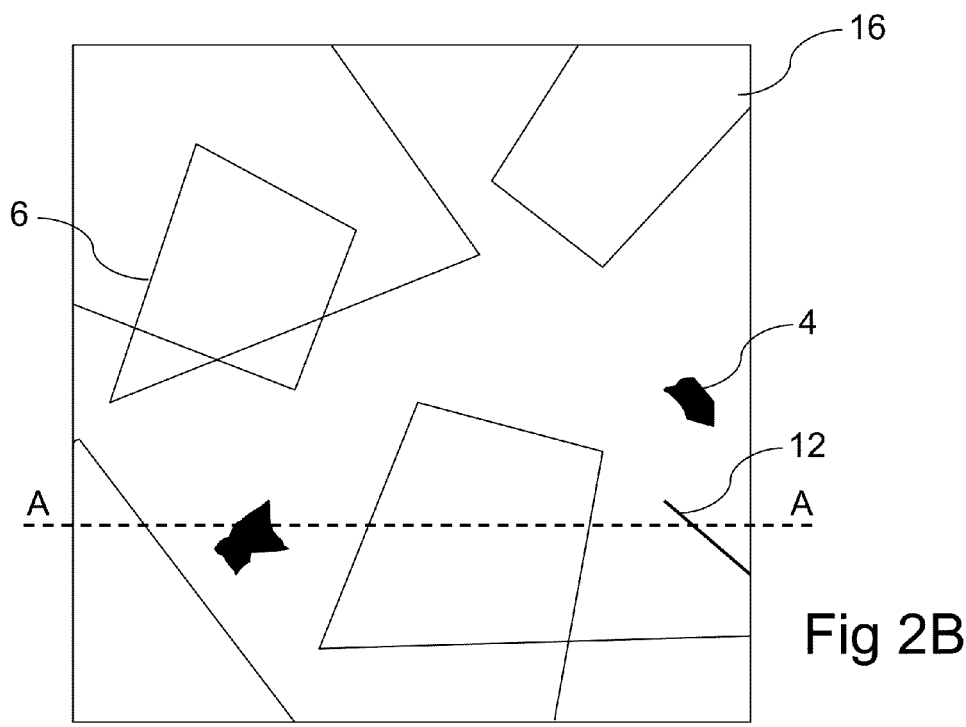

FIG. 2A shows a simulated PL image 16 of a multicrystalline silicon wafer, showing several different features including a number of recombination-active dislocation clusters 4 and grain boundaries 6, a crack 12, and a low lifetime region of impurity-rich silicon 8 along one edge. FIG. 2B shows a simulated PL image 16 of a second multicrystalline silicon wafer, again showing a number of recombination-active dislocation clusters 4 and grain boundaries 6, and a crack 12. It will be noticed that the dislocation clusters and grain boundaries are in different positions in the second wafer, and that the second wafer has no impurity-rich edge region, but that the crack 12 is at the same position. Consequently if the two PL images are combined, the crack will be enhanced relative to the other features.

Figure 3A:
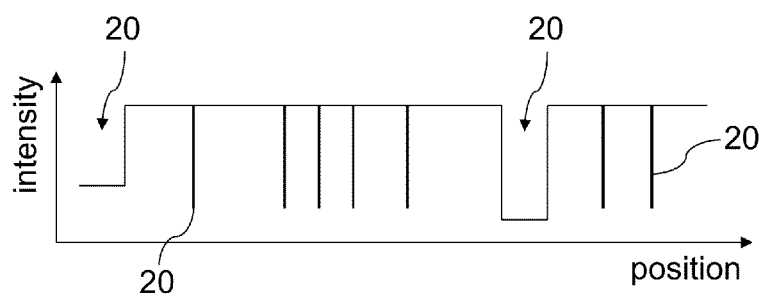
FIGS. 3A and 3B illustrate plots of PL intensity versus position along lines A-A at the same location on each of the FIG. 2A and FIG. 2B images.
Figure 3B:
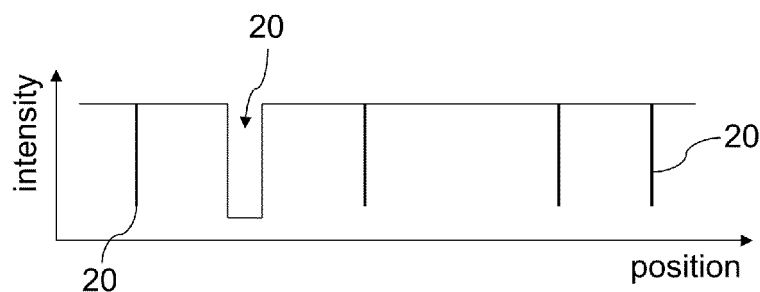
Figure 3C:
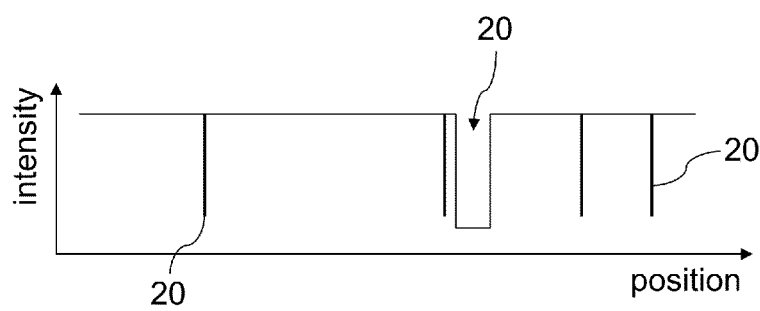
FIG. 3C illustrates a plot of PL intensity versus position for a third multicrystalline silicon wafer with a crack.
Figure 4:
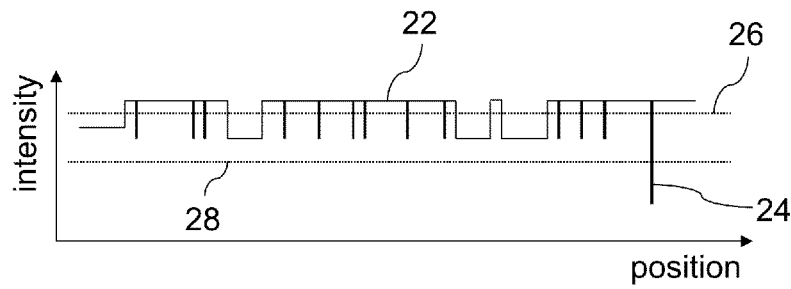
FIG. 4 illustrates a super-image obtained by combining the PL intensity line scans of FIGS. 3A to 3C.

To demonstrate this effect more concretely, the PL intensity along the line A-A in each of FIGS. 2A and 2B is presented in FIGS. 3A and 3B respectively, showing regions of lower intensity 20 associated with the various features. FIG. 3C shows a corresponding intensity line scan from a third sample wafer. The intensity line scans of FIGS. 3A to 3C are then combined by averaging to provide the 'super-image' intensity line scan 22 shown in FIG. 4, in which a strong signal 24 in the form of a low intensity region clearly emerges from the average signal level 26, indicative of a persistent feature which in this case is a systematic defect in the form of a crack occurring in substantially the same position in each sample. In certain embodiments a threshold signal level 28 is defined above and/or below the average signal level 26, beyond which (in absolute terms) a persistent feature will be flagged. Once a persistent feature is detected, an operator may be alerted to investigate the cause, which may for example be a fault with a wafer handling robot.

The intensity of PL emitted from a photovoltaic wafer or cell is, in broad terms, an indicator of the material quality, which has a strong effect on cell efficiency. Consequently the average signal level, or the 'background' signal level in regions excluding the persistent features, may also be useful for predicting operational characteristics of the sample cells, or of cells made from the sample wafers.

EXAMPLE 2

Figure 5A:
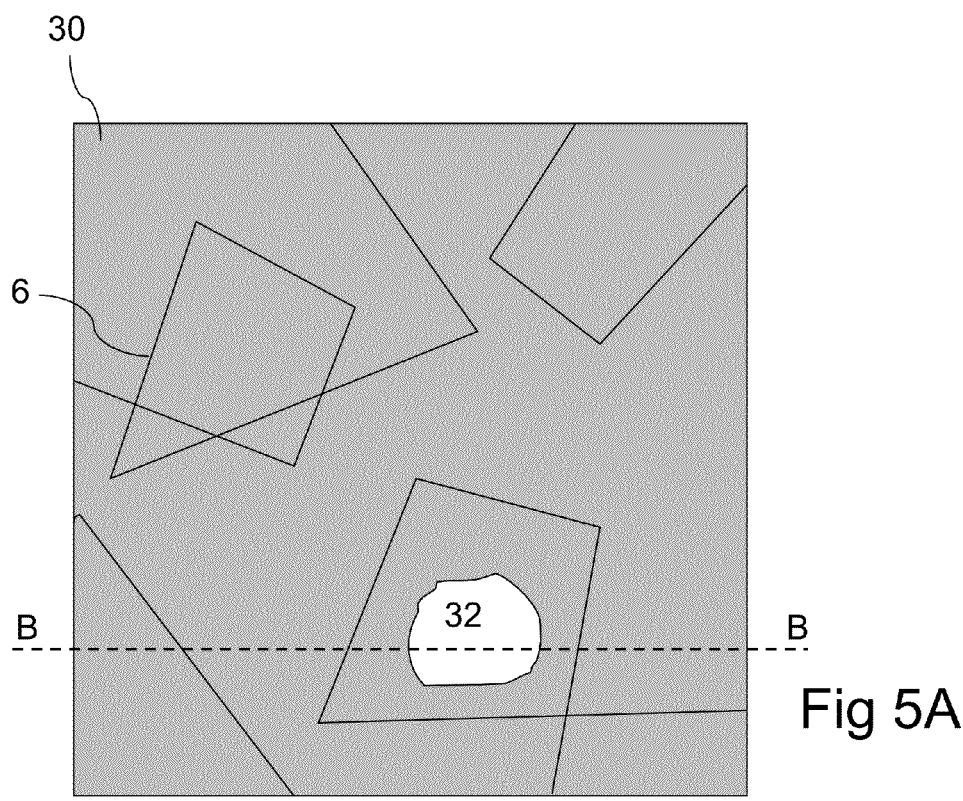
FIG. 5A shows a simulated reflection image of a multicrystalline silicon wafer.
Figure 5B:
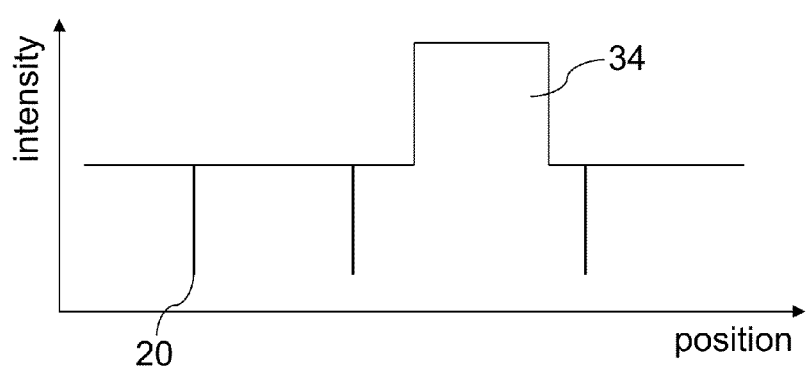
FIG. 5B illustrates a plot of reflection intensity versus position along line B-B on the FIG. 5A image.

FIG. 5A shows a simulated reflection image 30 of a multicrystalline silicon wafer, showing a number of grain boundaries 6 and a surface stain 32 of higher reflectance material. The optical intensity along the line B-B is presented in FIG. 5B, showing regions of lower intensity 20 associated with the grain boundaries and a region of higher intensity 34 associated with the surface stain. It will be appreciated that if the surface stain appears in substantially the same position in a number of samples, while the positions of the grain boundaries differ, the stain will clearly emerge as a region of higher intensity when images from a number of samples are combined to form a super-image.

EXAMPLE 3

Figure 6A:
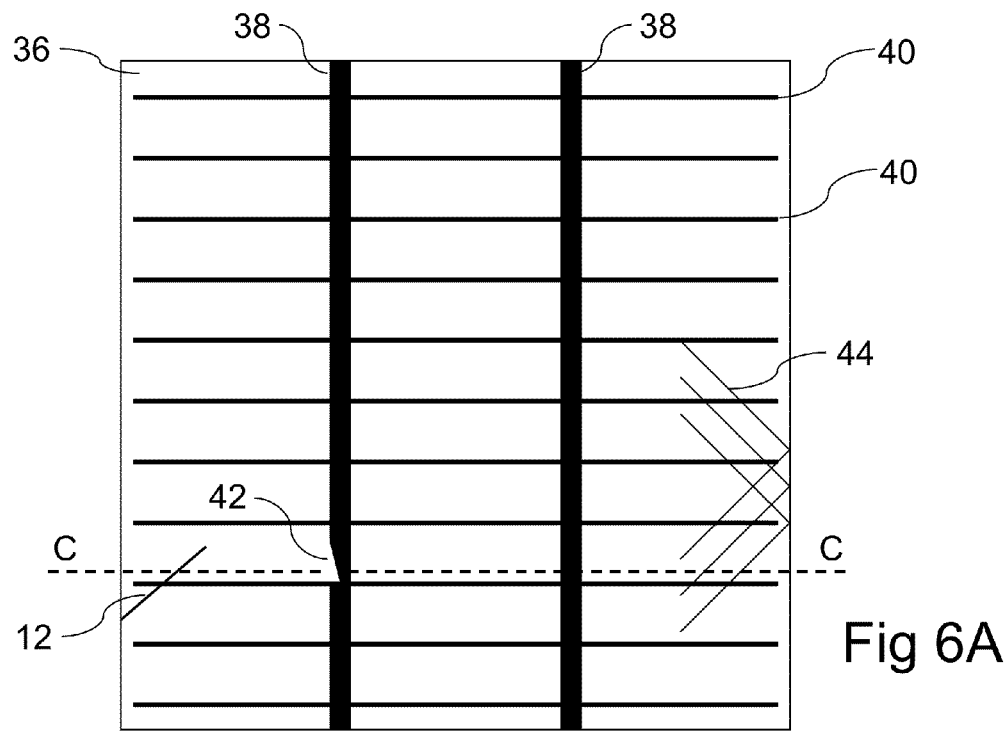
FIGS. 6A and 6B show simulated PL images of two different monocrystalline silicon photovoltaic cells, where each cell has a crack and a metallisation defect.
Figure 6B:
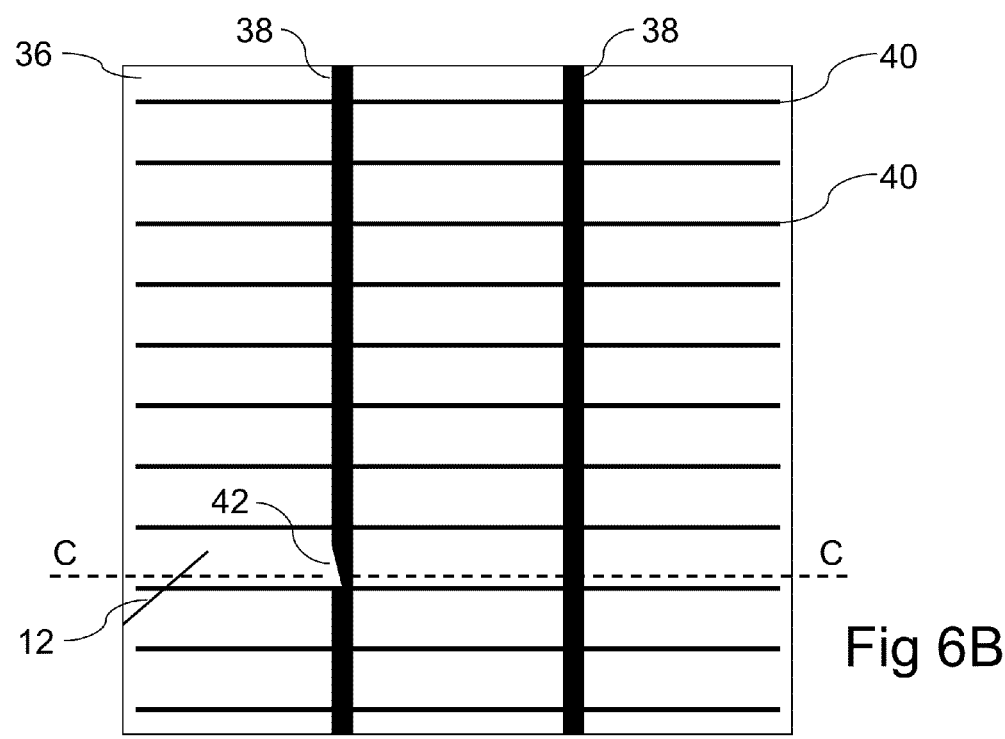
Figure 7A:
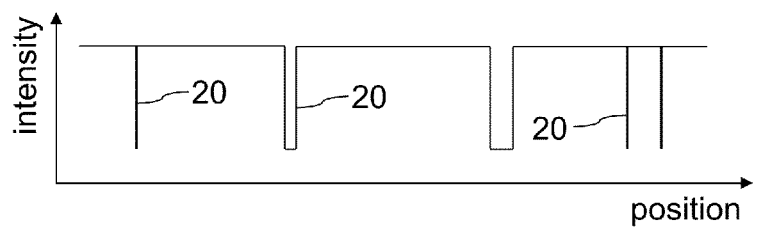
FIGS. 7A and 7B illustrate plots of PL intensity versus position along lines C-C at the same location on each of the FIG. 6A and FIG. 6B images.
Figure 7B:
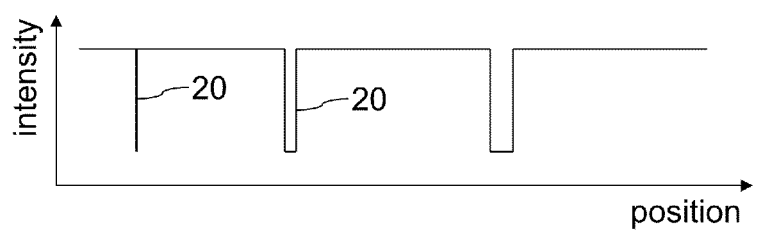
Figure 8A:
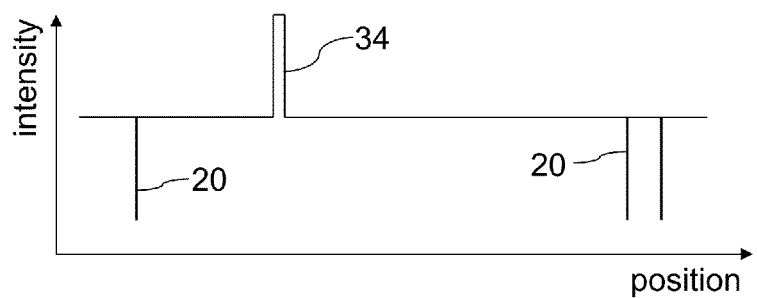
FIGS. 8A and 8B show corresponding plots of PL intensity versus position, corrected for the expected locations of the metal lines on the cells.
Figure 8B:
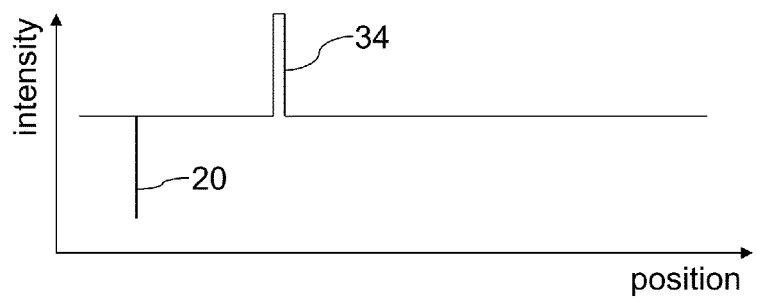
Figure 9:
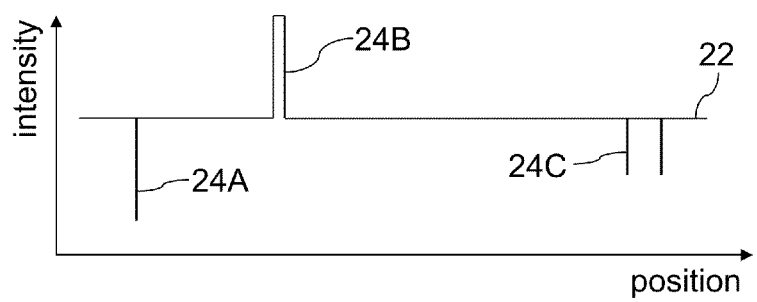
FIG. 9 illustrates a super-image obtained by combining the corrected PL intensity line scans of FIGS. 8A and 8B.

FIG. 6A shows a simulated PL image 36 of a monocrystalline silicon photovoltaic cell having a metal grid pattern with two bus bars 38 and numerous fingers 40 screen-printed on the front surface. The image also shows a crack 12 initiated perhaps by a piece of grit on the print screen, a defect 42 in one of the bus bars caused perhaps by a blockage on the print screen, and a set of slip lines 44 at one edge of the cell. FIG. 6B shows a simulated PL image 36 of a second monocrystalline silicon photovoltaic cell with essentially the same features except for an absence of slip lines. The PL intensity along the line C-C in each of FIGS. 6A and 6B is presented in FIGS. 7A and 7B respectively, showing regions of lower intensity 20 associated with the bus bars, the crack and the slip lines. Since the bus bars are known features, their expected contributions to the line scans can be removed to produce the corrected line scans presented in FIGS. 8A and 8B, which contain low intensity regions 20 associated with the crack and slip lines and a high intensity region 34 associated with the metallisation defect, i.e. a partial absence of the bus bar material. When the corrected line scans are combined by summing to provide the 'super-image' intensity line scan 22 shown in FIG. 9, it can be seen that the signals due to the cracks (24A) and the metallisation defects (24B) are enhanced relative to the signals due to the slip lines (24C) that occur in only one of the sample cells. It will be appreciated that the signals due to the cracks and metallisation defects will be further enhanced when images/line scans from additional sample cells contribute to the super-image, allowing these features to be identified as persistent, process-induced defects. In an alternative embodiment the 'uncorrected' line scans shown in FIGS. 7A and 7B are combined to form a super-image, from which the persistent features can be identified by ignoring or removing the expected contributions from the bus bars.

Figure 10:
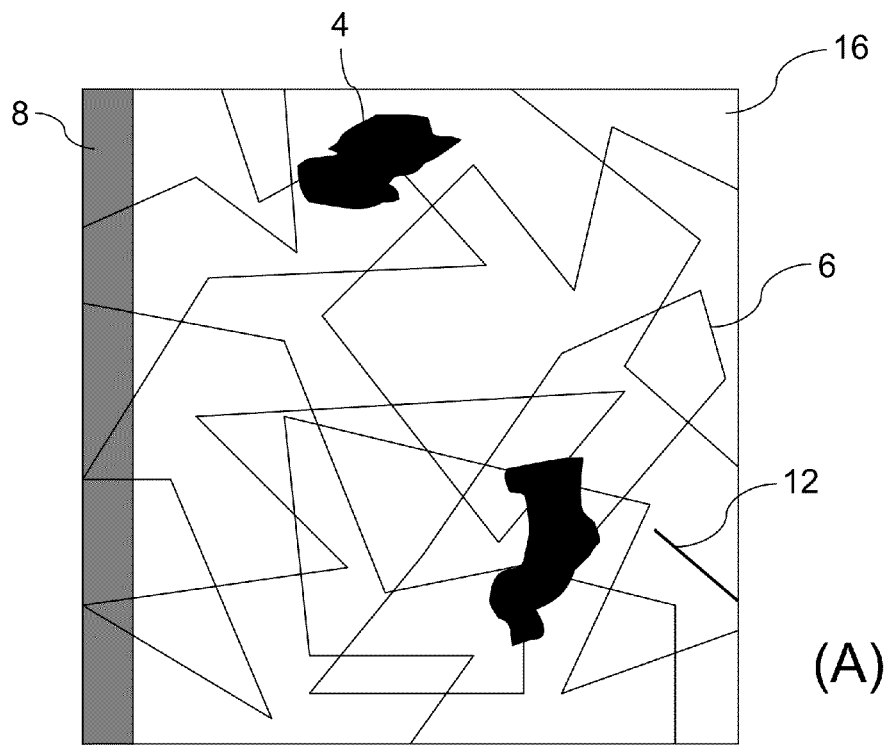
FIG. 10 illustrates misalignment between simulated PL images of two different multicrystalline silicon wafers.
Figure 10:
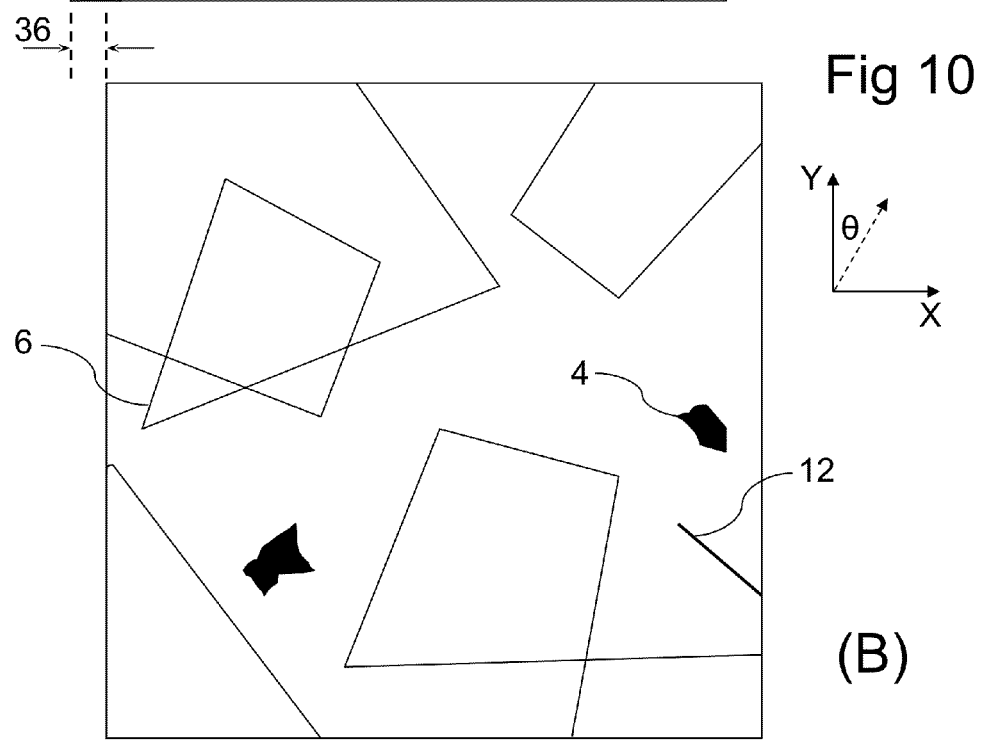

When combining or cumulating individual PL images to form a cumulative or super-image, the images should be carefully registered (i.e. aligned) or else persistent features such as repeated cracks will tend to be averaged out, making their detection more difficult. By way of example, FIG. 10 reproduces as (A) and (B) the simulated PL images shown in FIGS. 2A and 2B respectively, but with the images off-set by a distance 36 in the X direction to illustrate the wafers being placed in slightly different positions on a transport belt. Misalignment may also occur in Y and θ. It will be appreciated that when the images are summed the regions of reduced PL signal around the cracks will not be enhanced as they would be if the images were correctly aligned. Various image transformation or registration techniques applicable to complete or partial images of wafers or cells will be known to those skilled in the art, for example making use of wafer edges or the positions of known features such as the bus bars or laser-scribed wafer identification codes.

It will also be evident that the preferred embodiment can be utilised in a more subtle feedback situation. Where multiple variable parameters are available, the continual monitoring of regions allows for fine tuning of processes for optimal results.

Although the present invention has been described with particular reference to certain preferred embodiments thereof, variations and modifications of the present invention can be effected within the spirit and scope of the following claims.

The claims defining the invention are as follows:

1. A method for detecting systematic features in products being manufactured on a process line, said method comprising the steps of:
   (a) acquiring images of a plurality of said products, each image being of substantially the same area on each of said products;
   (b) combining said images to obtain a super-image;
   (c) processing said super-image to identify regions with strong signals; and
   (d) identifying said regions as being indicative of systematic features in said products.

2. A method for detecting systematic features in products being manufactured on a process line, said method comprising the steps of:
   (a) acquiring images of a plurality of said products, each image being of substantially the same area on each of said products;
   (b) combining said images to obtain a super-image;
   (c) processing said super-image to identify regions with strong signals;
   (d) comparing said regions with known features in said area; and
   (e) identifying those of said regions that do not correspond to said known features as being indicative of systematic features in said products.

3. A method according to claim 1, further comprising the step of:
   (e) prior to said combining step, correcting said images to remove known features in said area.

4. A method according to claim 1, wherein said combining step comprises summing, averaging or obtaining a median.

5. A method according to claim 1, wherein said regions with strong signals are identified by comparison with a predetermined threshold.

6. A method according to claim 1, wherein said images are photoluminescence images.

7. A method according to claim 1, wherein said images are electroluminescence images.

8. A method according to claim 1, wherein said images are reflection or transmission images in the visible or infrared spectral regions.

9. A method according to claim 1, wherein said method is performed at multiple stages in said process line, to identify stages in said process line where said systematic features are introduced.

10. A method according to claim 1, when used to detect systematic features in photovoltaic wafers, cells or modules.

11. A method according to claim 10, wherein said systematic features are cracks in said photovoltaic wafers, cells or modules.

12. A method according to claim 10, wherein said super-image is further processed to determine a background signal level in portions away from said regions with strong signals, and said background signal level is used to predict the performance of said photovoltaic wafers, cells or modules.

13. A method according to claim 1, wherein said images are combined in the Fourier, Discrete Cosine Transform, Hadamard or Wavelet domain.

14. A method according to claim 1, wherein said combining includes monitoring statistical variances from expected values for regions of said images.

15. A method according to claim 1, further comprising the step of aligning said images prior to said combining step.

16. A method according to claim 1, further comprising the step of identifying the type or nature of said systematic features.

17. A method according to claim 1, further comprising the step of taking action to remove the process cause of said systematic features.

18. A method for detecting process-induced defects in products being manufactured on a process line, said method comprising the steps of:
   (a) acquiring images of corresponding areas of a plurality of said products;
   (b) cumulating said images to produce a cumulative image; and
   (c) identifying signals in said cumulative image which exceed a predetermined threshold thereby determining said process-induced defects.

19. A method for detecting process-induced defects in products being manufactured on a process line, said method comprising the steps of:
   (a) acquiring images of corresponding areas of a plurality of said products;
   (b) cumulating said images to produce a cumulative image;
   (c) identifying signals in said cumulative image which exceed a predetermined threshold thereby determining one or more defect candidates; and
   (d) excluding from said candidates any known features, thereby determining said process-induced defects.

20. A method according to claim 18, further comprising the step of:
   (d) prior to said cumulating step, correcting said images by removing signals in each said image which correspond to any known features.

21. In a process line for manufacturing products, a method for detecting systematic features in products being manufactured on said process line, said method comprising the steps of:
  (a) acquiring images of a plurality of said products, each image being of substantially the same area on each of said products;
  (b) combining said images to obtain a super-image;
  (c) processing said super-image to identify regions with strong signals; and
  (d) identifying said regions as being indicative of systematic features in said products.

22. In a process line for manufacturing products, a method for detecting process-induced defects in products being manufactured on said process line, said method comprising the steps of:
  (a) acquiring images of corresponding areas of a plurality of said products;
  (b) cumulating said images to produce a cumulative image; and
  (c) identifying signals in said cumulative image which exceed a predetermined threshold thereby determining said process-induced defects.

23. An apparatus to implement the method according to claim 1.

24. An apparatus to implement the method according to claim 2.

25. An apparatus to implement the method according to claim 18.

26. An apparatus to implement the method according to claim 19.

27. A non-transitory computer readable medium with an executable program stored thereon, wherein the executable program causes an apparatus to implement the method according to claim 1.

28. A non-transitory computer readable medium with an executable program stored thereon, wherein the executable program causes an apparatus to implement the method according to claim 2.

29. A non-transitory computer readable medium with an executable program stored thereon, wherein the executable program causes an apparatus to implement the method according to claim 18.

30. An article of manufacture comprising a computer usable medium having a computer readable program code configured to implement the method according to claim 19.

* * * * *